(12) United States Patent
Wengel et al.

(10) Patent No.: US 7,282,492 B2
(45) Date of Patent: Oct. 16, 2007

(54) INSECTICIDAL COMPOSITION HAVING IMPROVED STORAGE STABILITY

(75) Inventors: Anita Wengel, Lemvig (DK); Vita Nielsen, Lemvig (DK)

(73) Assignee: Cheminova A/S, Lemvig (DK)

( * ) Notice: Subject to any disclaimer, the term of this patent is extended or adjusted under 35 U.S.C. 154(b) by 744 days.

(21) Appl. No.: 10/474,045

(22) PCT Filed: May 2, 2002

(86) PCT No.: PCT/DK02/00285

§ 371 (c)(1),
(2), (4) Date: Oct. 15, 2003

(87) PCT Pub. No.: WO02/089574

PCT Pub. Date: Nov. 14, 2002

(65) Prior Publication Data

US 2004/0116389 A1    Jun. 17, 2004

(30) Foreign Application Priority Data

May 7, 2001   (DK) .................... 2001 00708

(51) Int. Cl.
*A01N 57/12*    (2006.01)

(52) U.S. Cl. ..................... 514/119; 424/405
(58) Field of Classification Search ........... 514/461, 514/119

See application file for complete search history.

(56) References Cited

U.S. PATENT DOCUMENTS

| | | | | |
|---|---|---|---|---|
| 3,090,719 A | 5/1963 | Pinamonti | ........ | 164/22 |
| 3,278,369 A | 10/1966 | Haering | ........ | 167/22 |
| 4,147,781 A * | 4/1979 | Hurt | ........ | 514/113 |
| 4,892,866 A | 1/1990 | Itzel et al. | ........ | 514/119 |
| 5,234,919 A | 8/1993 | Roberts | ........ | 514/119 |
| 5,547,918 A | 8/1996 | Newton et al. | ........ | 504/116 |

FOREIGN PATENT DOCUMENTS

| | | |
|---|---|---|
| GB | 1043006 | 9/1966 |
| GB | 2050170 | 1/1981 |

* cited by examiner

*Primary Examiner*—Neil S. Levy
(74) *Attorney, Agent, or Firm*—Jacobson Holman PLLC

(57) ABSTRACT

An insecticidal composition having improved storage stability is disclosed. Said insecticidal composition comprises Dimethoate stabilized with maleic anhydride. Also a process for the control of insects is disclosed, wherein the insecticidal composition, possibly following a dilution, is apportioned to an area, in which crops are grown.

12 Claims, No Drawings

INSECTICIDAL COMPOSITION HAVING IMPROVED STORAGE STABILITY

This is a nationalization of PCT/DK02/00285 filed May 2, 2002 and published in English.

The present invention relates to an insecticidal composition having improved storage stability and containing Dimethoate as an active compound as well as to a process for the control of insects. The insecticidal composition according to the invention is particularly useful for the control of insect pests, such as sucking and chewing insects, within areas cultivated with agricultural crops and plantation crops.

Dimethoate, chemically termed as O,O-dimethyl S-methyl carbamoyl methyl phosphorous dithioate, is a well-known compound for the control of undesired insects. It is primarily used to control chewing and sucking insects attacking agricultural and plantation crops, and it works both systemically and by contact. When using Dimethoate, a mayor disadvantage is that the compound is thermally unstable and, at temperatures above approximately 50° C., it may decompose uncontrollably and, at worst, result in explosions. Even at lower temperatures, Dimethoate will decompose and lead to its activity dropping. Therefore, it is essential to be able to stabilize Dimethoate formulations so as to withstand even long-term storage without loss of activity, particularly in warm climatic surroundings.

On standing, Dimethoate will degrade into the corresponding S-methyl isomer according to the following mechanism:

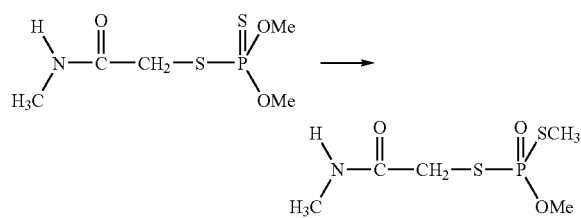

S-methyl isomer has proven toxic to mammals and, hence, it is undesirable in the end product.

Several formulations wherein Dimethoate has been stabilized with various stabilizers are described in the prior art. Thus, U.S. Pat. No. 3,090,719 discloses stabilizing Dimethoate formulations with aromatic hydrocarbons, aliphatic ketones, cyclic ketones (also known as cycloparaffinic ketones), acetates of primary alcohols, glycol ether acetates and tri-alkyl phosphoric esters.

U.S. Pat. No. 5,234,919 discloses stabilized formulations containing Dimethoate, in which a solvent system comprising a lower alkyl alcohol and a lower alkyl acetate ester is used.

In U.S. Pat. No. 4,892,866, cyclopropene fatty acids are used as stabilizers for Dimethoate and, in GB Patent No. 2050170-A the use of various organic acids in Dimethoate formulations is described, whereas GB Patent No. 1043006 relates to the use of various anhydrides, acetic anhydrides, propionic anhydrides and butyric anhydrides in particular, for the stabilization of formulations comprising Dimethoate.

U.S. Pat. No. 3,278,369 discloses emulsion concentrates of Dichlorvos, an organophosphate insecticidal, stabilized with for instance acetic anhydride or maleic anhydride. As it appears from Example 2 of said publication, acetic anhydride results in a better stabilizing effect than maleic anhydride.

The object of the present invention is to provide insecticidal compositions having improved storage stability even at temperatures above normal ambient temperature. Sufficient storage stability is essential in connection with commercial pesticides, and reduced degradation of the products on standing before the final use is financially very advantageous.

It has now been established that it is possible to stabilize Dimethoate against thermal degradation by means of maleic anhydride. Thus, the present invention relates to an insecticidal composition in which Dimethoate has been stabilized with maleic anhydride.

The invention also relates to a process for the control of insects, said process being characterized in that an insecticidal composition according to the invention, possibly following a dilution, is apportioned to an area, in which crops are grown, in an amount adequate to at least impede the growth of insects.

As shown in the following examples, maleic anhydride has a considerably better stabilizing effect than acetic anhydride. In view of the technical teaching derivable from U.S. Pat. No. 3,278,369 in connection with a related compound, it must be considered surprising that maleic anhydride has a significantly better stabilizing effect on Dimethoate in comparison with a corresponding amount of acetic anhydride. Compared to acetic anhydride, maleic anhydride may therefore be used in smaller amounts to stabilize Dimethoate formulations without jeopardizing the stability in connection with long-term standing, even at high temperatures. In addition to the improved stabilizing effect of maleic anhydride, also the degree of obnoxious smell is lower both during the manufacturing process and when in use than is the case with acetic anhydride.

The insecticidal composition according to the invention preferably contains 0.1 to 20 parts by weight maleic anhydride, calculated on the basis of 100 parts by weight Dimethoate. The use of maleic anhydride in a quantity below 0.1 parts by weight may be appropriate in certain formulations, since no lower limit for the stabilizing effect of maleic anhydride has been established. However, usually a concentration above 0.1 parts by weight maleic anhydride is preferred to ensure a sufficiently stabilized durability. In certain cases, it may be appropriate to use a quantity of maleic anhydride in a formulation above 20 parts by weight, since no upper limit for the stabilizing effect has been established. Generally, however, a maleic anhydride content of up to 20 parts by weight for each 100 parts by weight Dimethoate should be sufficient to ensure a high storage stability. More preferably, the insecticidal composition contains 1 to 15 parts by weight maleic anhydride and, most preferably, the insecticidal composition contains 2 to 10 parts by weight maleic anhydride, calculated on the basis of 100 parts by weight Dimethoate.

The insecticidal, composition according to the invention may be formulated in many different ways to obtain the storage stability effect. For instance, the insecticidal composition may be formulated as a solid preparation containing particulate Dimethoate and maleic anhydride only.

However, usually it is preferred, to formulate Dimethoate and maleic anhydride together with at least one further component. Said at least one component may be another biologically active compound or a compound that is inert in relation to Dimethoate. Inert components may be solid or liquid and either organic or inorganic. Whenever the component is inert in relation to Dimethoate, the at least one further component is particularly suitable to dissolve, disperse or emulsify Dimethoate.

The insecticidal compositions according to the invention may be prepared for instance in the form of water or oil based solutions, powders, dusting materials, pastes, aqueous or oil based suspensions, emulsifiable concentrates, micro emulsions, micro capsules, granules and water-dispersible granules. The choice of formulation type highly depends on the forthcoming application. In one embodiment of the present invention, the insecticidal composition is formulated as a concentrate to be diluted by a suitable diluent before use. Particularly, it is preferred to formulate the insecticidal composition as an emulsifiable concentrate.

A list of typical components for a liquid formulation would include inter alia mineral oils, aliphatic, cyclic, and aromatic carbon hydride compounds, e.g. xylene, paraffin, tetra-hydro napthalene, alkylated napthalenes or derivative compounds thereof, alkylated benzenes as well as derivative compounds thereof, aliphatic, cyclic., and aromatic alcohols, cyclo-hexanon or highly polar solvent s.

For certain formulation types it is desirable to add one or more surface-active compounds foreseen to ensure the physical stabilization of the formulations and to make sure that the formulations are being quickly absorbed by the crops/plants on which they are to be used. The surface-active compounds may be either ionic or non-ionic. A list of suitable surface-active compounds would include salts of alkali metal, alkaline earth metal, and ammonium salts of aromatic sulphonic acids, e.g. ligno acid, phenol acid, naphthalene acid, or dibutyl napthalene sulphonic acid as well as fatty acids; alkyl acids, alkyl aryl sulphonic acids; salts of fatty alcohol sulphates; condensates of sulphonated naphthalenes and derived compounds comprising formaldehyde; condensates of naphthalene or naphthalene sulphonic acids with phenol and formaldehyde as well as fatty alcohol/ethylene oxide condensates and sorbitol esters.

Powders and dusting materials may be obtained by mixing or grinding Dimethoate and maleic anhydride, possibly together with one or more solid excipients, or by saturating solid excipients with solutions of maleic anhydride and Dimethoate in volatile solvents, evaporating the solvents and, possibly, grind the products into powders. Granules may be obtained by granulating powders prepared as described above or by having Dimethoate and maleic anhydride be absorbed on solid excipients. Examples of suitable solid excipients are alumino-silicate, talcum, calcinated magnesium oxide, diatomite and clay types, such as kaolin and bentonite.

If desired, the insecticidal compositions according to the invention may also contain anti-foam agents, protective colloids, thickenings, UV-absorbants, dyes, corrosion inhibitors, and other pesticide-active compounds.

The insecticidal compositions according to the invention comprise solid and liquid formulations for immediate use by being spread onto an area, for which insect control is wanted, and highly concentrated liquid formulations that are usually diluted before use.

The concentrates may contain up to 95% by weight Dimethoate based on the weight of the formulation, preferably, between. 10 and 70% by weight and, more preferably, between 20 and 60% by weight. Following a dilution with a suitable composition, usually water, which will often be chosen, before use, the Dimethoate content will vary depending on the relevant purpose, typically, however, the dosage will correspond to an apportion of up to 1 kg Dimethoate a hectare, preferably, up to 0.5 kg a hectare.

The formulations according to the invention are applicable for the control of quite a number of insects, primarily sucking and chewing insects, in areas grown with agricultural and plantation crops in particular, but may advantageously be used in other places infected with undesired insects, e.g. areas where insects live or their eggs hatch.

The following examples illustrate methods of carrying out the invention but do in no way represent delimitations thereof:

EXAMPLE 1

Three emulsifiable concentrates (Ia, Ib and Ic) containing. Dimethoate were prepared by mixing the components listed below in the amounts stated. Said amounts are parts by weight.

| Components | Ia | Ib | Ic |
|---|---|---|---|
| Dimethoate | 38.8 | 38.7 | 38.7 |
| Cyclohexanone | 43.2 | 43.1 | 43.1 |
| Xylene | 13.2 | 12.5 | 12.5 |
| Berol 992 (alcoxylated alcohol - emulsifier) | 4.8 | 4.75 | 4.75 |
| Maleic anhydride | 0 | 0 | 0.95 |
| Acetic anhydride | 0 | 0.95 | 0 |

The formulation Ia does not contain any compound for the stabilization of Dimethoate, whereas in formulation Ib acetic anhydride is used as a stabilizer. The formulations Ia and Ib are not according to the invention but serve as comparison examples to formulation Ic (according to the invention).

The formulations were stored at different temperatures for various periods of time, whereupon the pro rata share of Dimethoate degradation was determined. The results are shown in Table 1.

TABLE 1

| % degradation of Dimethoate | | | | | | | | |
|---|---|---|---|---|---|---|---|---|
| 14 days at 54° C. | | | 3 months at 40° C. | | | 1 year at 30° C. | | |
| Ia | Ib | Ic | Ia | Ib | Ic | Ia | | Ic |
| 8.0 | 2.4 | 1.2 | 7.8 | 7.2 | 1.3 | 9.1 | | 5.8 |

The results of Table 1 show that after having been stored for 14 days at 54° C., Dimethoate had been stabilized twice as effectively with maleic anhydride as with acetic anhydride. When stored for 3 months at 40° C., the storage stability obtained was more than 5 times better with maleic anhydride as with acetic anhydride. After having been stored for 1 year at 30° C., the product still shows a low degradation in comparison with the product without any stabilizer.

EXAMPLE 2

A number of formulations were prepared by the same process as in Example 1 but having various anhydride contents, viz. 0.5% by weight, 1% by weight, 2% by weight, and 3% by weight based on the weight of the formulation. Said concentrations of maleic anhydride correspond to a content of 1.2 parts by weight, 2.5 parts by weight, 4.9 parts by weight and 7.4 part by weight maleic anhydride, respectively, for 100 parts by weight Dimethoate. For stability comparison reasons, corresponding formulations were prepared in which the maleic anhydride had been replaced by acetic anhydride. The results appear from Table 2.

TABLE 2

| Stabilizer content in the formulation | % degradation of Dimethoate | | | |
| --- | --- | --- | --- | --- |
| | Acetic anhydride | | Maleic anhydride | |
| | 14 days at 54° C. | 3 months at 40° C. | 14 days at 54° C. | 3 months at 40° C. |
| 0.5% by weight | 4.2 | 13.5 | 4.1 | 3.4 |
| 1% by weight | 2.4 | 7.2 | 1.2 | 1.3 |
| 2% by weight | 2.1 | 4.3 | — | 1.1 |
| 3% by weight | 1.6 | 4.1 | 0 | 1.1 |

The results of Table 2 show that a stabilizing effect is demonstrable already at a maleic anhydride content of 0.5% by weight. In comparison with acetic anhydride, the stabilizing effect of maleic anhydride in the low concentration of 0.5% by weight when stored for 3 months at 40° C. is particularly evident. The stabilizing effect of maleic anhydride improves upon an increased concentration in the formulations until an apparently complete degradation inhibition is obtained after a relatively short-term storage for 14 days at 54° C. Upon storage for 3 months at 40° C. a maximally possible stabilizing seems obtainable with a maleic anhydride concentration of 2% by weight, since adding an increased amount of maleic anhydride does not result in a further lowering of the amount of degraded Dimethoate.

EXAMPLE 3

A concentrate without any emulsifier was prepared by initially dissolving 547 g Dimethoate in 444 g cyclohexanon. Subsequently, as a stabilizer, 1% by weight maleic anhydride was admixed, corresponding to 1.6 parts by weight maleic anhydride based on 100 parts by weight Dimethoate. Comparable compounds containing 3% by weight and 5% by weight maleic anhydride were prepared, corresponding to 4.9 part by weight and 8.2 parts by weight maleic anhydride, respectively, based on 100 parts by weight Dimethoate. For stability comparison reasons also a compound without any stabilizer was prepared.

The compounds prepared were stored for 14 days at 54° C., whereupon the pro rata share of degradation was determined. The results are shown in Table 3.

TABLE 3

| Stabilizer content in the formulation | Pro rata degradation of Dimethoate after 14 days at 54° C. |
| --- | --- |
| 0 | 9.0 |
| 1% by weight | 1.7 |
| 3% by weight | 1.2 |
| 5% by weight | 0.7 |

As it appears from Table 3, if the stabilizer content is increased, a liquid composition containing Dimethoate, a solvent (cyclo-hexanon) and a stabilizer (maleic anhydride) shows a lower degradation and thus prolonged durability. No upper limit for the maximally obtainable stabilizing has been established.

The invention claimed is:

1. An insecticidal composition having improved storage stability and containing dimethoate, wherein the dimethoate is stabilized by maleic anhydride.

2. An insecticidal composition according to claim 1, wherein the composition contains 0.1 to 20 parts by weight of maleic anhydride, calculated on the basis of 100 parts by weight of dimethoate.

3. An insecticidal composition according to claim 1, wherein the composition contains 1 to –15 parts by weight of maleic anhydride, calculated on the basis of 100 parts by weight of dimethoate.

4. An insecticidal composition according to claim 1, wherein the composition contains 2 to 10 parts by weight maleic anhydride, calculated on the basis of 100 parts by weight of dimethoate.

5. An insecticidal composition according to claim 1, wherein the composition is prepared as a concentrate to be diluted with a suitable diluent before use.

6. An insecticidal composition according to claim 5, wherein the concentrate contains an emulsifier and a solvent so as to obtain an emulsifiable concentrate.

7. An insecticidal composition according to claim 5, wherein the content of dimethoate is up to 95% by weight based upon the weight of the formulation.

8. An insecticidal composition according to claim 7, wherein the content of dimethoate is between 10 and 70% by weight based upon the weight of the formulation.

9. An insecticidal composition according to claim 8, wherein the content of dimethoate is between 20 and 60% by weight based upon the weight of the formulation.

10. A process for the control of insects, comprising the steps of:
    diluting an insecticidal composition according to claim 1, with a suitable diluent, and
    applying said insecticidal composition to an area in which crops are grown, in an amount adequate to at least impede the growth of insects.

11. A process according to claim 10, wherein the insecticidal composition is applied to the area, in which crops are grown, in an amount of up to 1 kg dimethoate a hectare.

12. A process according to claim 10, wherein the insecticidal composition is applied to the area, in which crops are grown, in an amount of up to 0.5 kg dimethoate a hectare.

* * * * *